United States Patent
LeBaron et al.

(10) Patent No.: US 10,463,862 B2
(45) Date of Patent: *Nov. 5, 2019

(54) IMPLANTABLE RELAY MODULE

(71) Applicant: Micron Devices LLC, Pompano Beach, FL (US)

(72) Inventors: Richard LeBaron, Miami Beach, FL (US); Laura Tyler Perryman, Pompano Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/008,245

(22) Filed: Jun. 14, 2018

(65) Prior Publication Data

US 2018/0289972 A1    Oct. 11, 2018

Related U.S. Application Data

(63) Continuation of application No. 15/807,023, filed on Nov. 8, 2017, now Pat. No. 10,179,244, which is a (Continued)

(51) Int. Cl.
*A61N 1/372*    (2006.01)
*A61N 1/378*    (2006.01)
(Continued)

(52) U.S. Cl.
CPC ...... *A61N 1/37229* (2013.01); *A61B 17/3468* (2013.01); *A61N 1/36125* (2013.01); *A61N 1/3787* (2013.01); *A61N 1/37223* (2013.01)

(58) Field of Classification Search
None
See application file for complete search history.

(56) References Cited

U.S. PATENT DOCUMENTS 5,383,915 A  *  1/1995  Adams ............... A61N 1/37282
                                                       128/903
8,855,789 B2 * 10/2014  Jacobson ............. A61N 1/3708
                                                       607/119
(Continued)

FOREIGN PATENT DOCUMENTS

WO    WO 2008/051913    5/2008
WO    WO2012103519      8/2012
(Continued)

OTHER PUBLICATIONS

International Search Report and Written Opinion for International Application No. PCT/US2017/013718 dated Mar. 30, 2017.

*Primary Examiner* — Kennedy Schaetzle
(74) *Attorney, Agent, or Firm* — Fish & Richardson P.C.

(57) ABSTRACT

A passive implantable relay module includes a first coupler arm configured to wirelessly receive electromagnetic energy radiated through electric radiative coupling from a transmitting antenna located outside a subject's body; a second coupler arm; and a connector portion comprising a first metal core and a first dielectric coating surrounding the first metal core, the connector portion configured to connect the first coupler arm to the second coupler arm such that when the passive implantable relay module is implanted inside the subject's body and the transmitting antenna initiates wireless energy transfer to the first coupler arm via non-inductive coupling, electromagnetic waves carrying the electromagnetic energy received at the first coupler arm propagate along the first metal core to arrive at the second coupler arm, where the electromagnetic energy arriving is wirelessly transferred, again via non-inductive coupling, to a receiving antenna on a passive wireless neural stimulator device.

21 Claims, 22 Drawing Sheets

Related U.S. Application Data continuation of application No. PCT/US2017/013718, filed on Jan. 17, 2017.

(60) Provisional application No. 62/279,361, filed on Jan. 15, 2016.

(51) Int. Cl.
*A61N 1/36* (2006.01)
*A61B 17/34* (2006.01)

(56) References Cited

U.S. PATENT DOCUMENTS

| | | | |
|---|---|---|---|
| 2005/0234360 A1* | 10/2005 | Richardson | A61B 5/0006 600/510 |
| 2006/0009831 A1 | 1/2006 | Lau et al. | |
| 2007/0179550 A1* | 8/2007 | Dennis | A61N 1/025 607/36 |
| 2007/0233204 A1 | 10/2007 | Lima et al. | |
| 2008/0269863 A1 | 10/2008 | Alexander et al. | |
| 2010/0042109 A1 | 2/2010 | Barker | |
| 2010/0286791 A1 | 11/2010 | Goldsmith | |
| 2012/0059389 A1* | 3/2012 | Larson | A61N 1/056 606/129 |
| 2012/0095531 A1* | 4/2012 | Derbas | A61N 1/0553 607/68 |
| 2012/0130450 A1 | 5/2012 | Vajha et al. | |
| 2013/0079849 A1 | 3/2013 | Perryman et al. | |
| 2014/0031837 A1 | 1/2014 | Perryman et al. | |
| 2014/0031902 A1* | 1/2014 | Mashiach | A61N 1/0558 607/62 |
| 2015/0127068 A1 | 5/2015 | Simon et al. | |
| 2015/0297900 A1 | 10/2015 | Perryman et al. | |

FOREIGN PATENT DOCUMENTS

| | | |
|---|---|---|
| WO | WO2012138782 | 10/2012 |
| WO | WO2013019757 | 2/2013 |
| WO | WO2013025632 | 2/2013 |
| WO | WO2013040549 | 3/2013 |
| WO | WO2015175572 | 11/2015 |

\* cited by examiner

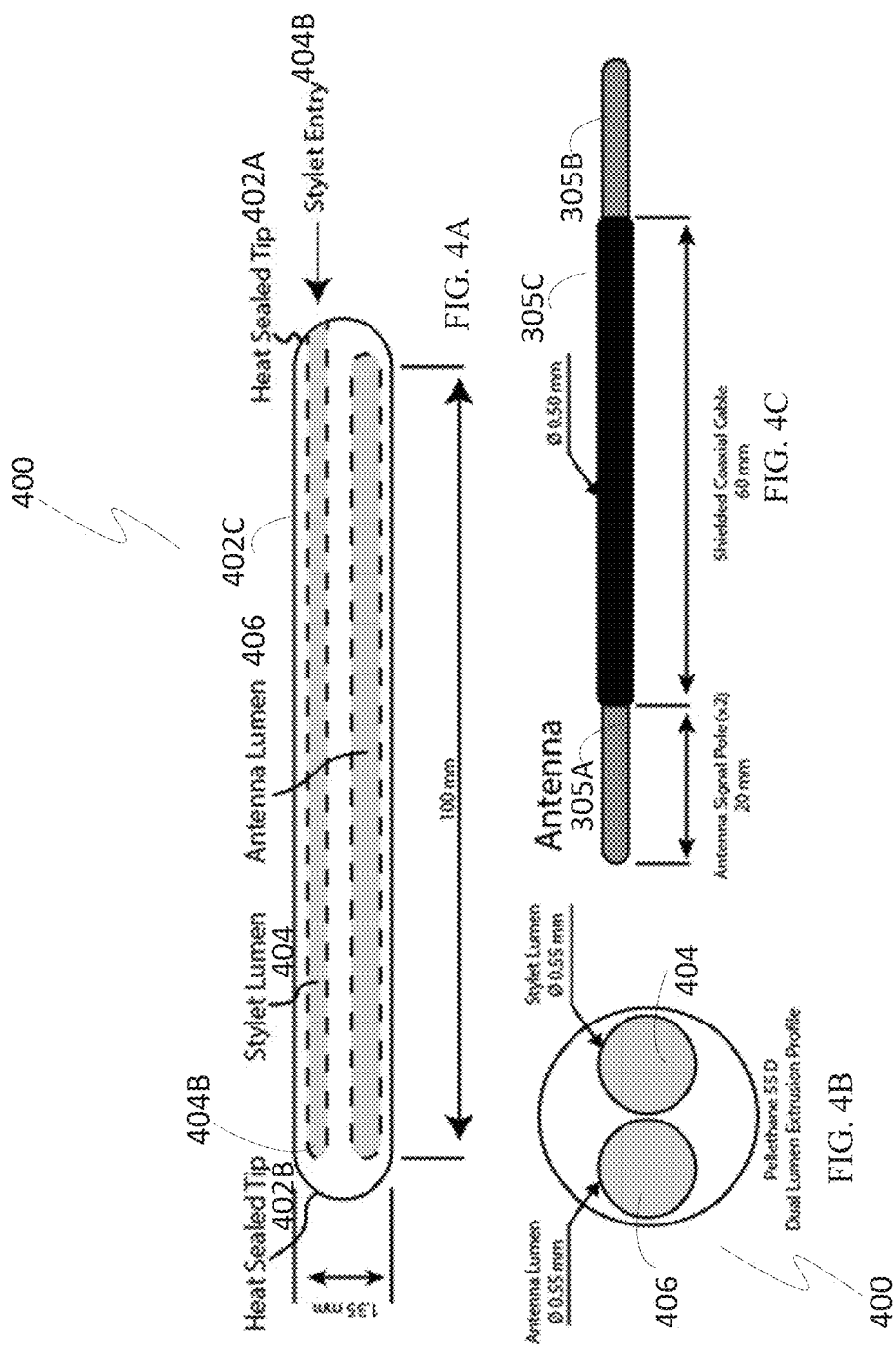

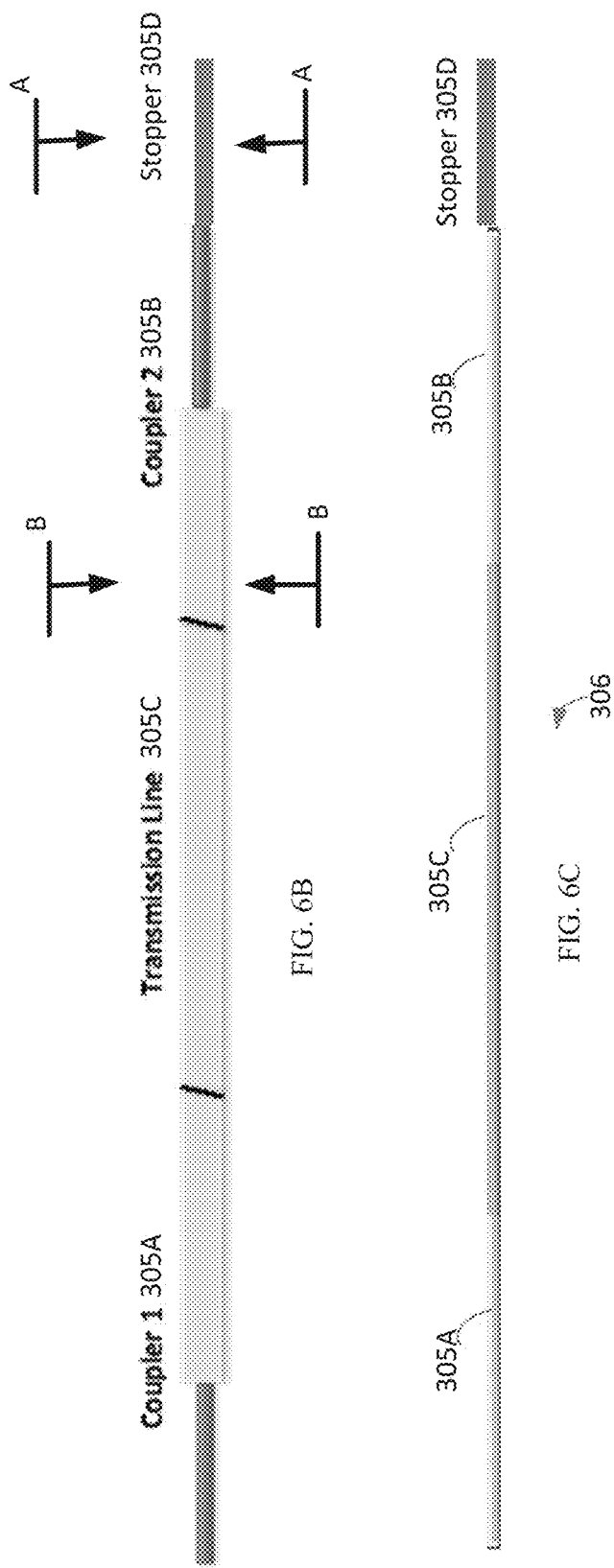

IMPLANTABLE RELAY MODULE

CROSS-REFERENCE TO RELATED APPLICATIONS

This application is a continuation of U.S. Ser. No. 15/807,023, filed Nov. 8, 2017, which is a continuation of International Application PCT/US2017/013718, filed Jan. 17, 2017, which claims priority to U.S. Provisional Application Ser. No. 62/279,361, filed on Jan. 15, 2016. The contents of all of which are incorporated in their entirety.

TECHNICAL FIELD

This application relates generally to a relay module to couple energy from an antenna to an implanted stimulator device.

BACKGROUND

Modulation of excitable tissue in the body by electrical stimulation has become an important type of therapy for patients with chronic disabling conditions, including pain, movement initiation and control, involuntary movements, vascular insufficiency, heart arrhythmias and various other modalities. A variety of therapeutic intra-body electrical stimulation techniques can be utilized to provide therapeutic relief for these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

SUMMARY

In one aspect, some implementations provide a passive implantable relay module that includes a first coupler arm configured to wirelessly receive electromagnetic energy radiated through non-inductive coupling from a transmitting antenna located outside a subject's body; a second coupler arm; and a connector portion comprising a first metal core and a first dielectric coating surrounding at least portions of the first metal core, the connector portion configured to connect the first coupler arm to the second coupler arm and to transport the received electromagnetic energy from the first coupler arm to the second coupler arm such that when the passive implantable relay module is implanted inside the subject's body and the transmitting antenna initiates wireless energy transfer to the first coupler arm through non-inductive coupling, electromagnetic waves carrying the electromagnetic energy received at the first coupler arm propagate along the first metal core to arrive at the second coupler arm, where the electromagnetic energy arriving is wirelessly transferred, again through non-inductive coupling, to a receiving antenna on a passive wireless neural stimulator device that has been implanted inside the subject to be solely powered wirelessly.

Implementations may include one or more of the following features:

The metal core may be sized and shaped to run a longitudinal length that is approximately a half wavelength of the electromagnetic waves propagating thereon from the first coupler arm to the second coupler arm. The metal core may be sized and shaped to run a longitudinal length that is approximately multiples of half wavelength of the electromagnetic waves propagating thereon from the first coupler arm to the second coupler arm. The metal core may be sized and shaped to run a particular longitudinal length such that the electromagnetic energy that has arrived at the second coupler arm is no less than 50% of the electromagnetic energy that has been received at the first coupler arm. The electromagnetic energy that has arrived at the second coupler arm may be at least 10 times greater than when the first metal core is absent.

The connector portion may have an inner diameter that is no bigger than 1.8 mm. The connector portion may be sized and shaped to snake through a tubing within a lumen that is no bigger than 1.8 mm or under when the passive implantable relay is implanted inside the subject such that (i) the second coupler arm is placed substantially parallel to the receiving antenna on the passive implantable neural stimulator device and (ii) the second coupler arm is positioned to wirelessly transmit the electromagnetic energy, through non-inductive coupling, to the receiving antenna on the passive wireless neural stimulator device that has been implanted inside the subject, wherein the electromagnetic energy has arrived from the connector portion.

The connector portion may include a second metal core sized and shaped to run a longitudinal length comparable to that of the first metal core, and wherein a distal end of the first metal core and a proximal end of the second metal core are positioned to form a parallel overlap but without contacting each other such that when the connector portion is placed inside a magnet where the subject is taking an magnetic resonance scan, heating caused by electrical charges accumulated along the connector portion during the magnetic resonance scan is substantially reduced than otherwise. The parallel overlap may run approximately a half wavelength of the electromagnetic waves carrying the electromagnetic energy received at the first coupler arm and from the transmitting antenna located outside the subject's body.

The metal core may be made of copper, or gold-plated stainless steel. The dielectric coating may be made of PolyEtherEtherKetone (PEEK). The connector portion may be without an outer shield that is made of metal. The connector portion may further include an outer shield that is made of metal, the outer shield enclosing at least portions of the dielectric coating.

The first coupler arm may include a first center conductor region, wherein the second arm may also include a second center conductor region. The first center conductor region may be aligned with the transmitting antenna such that linearly polarized electric field is captured by the first center conductor region. The second center conductor region may be aligned with the transmitting antenna such that linearly polarized electric field is captured by the second center conductor region. The first center conductor region and the second center conductor region may be of the same length of approximately 5 mm.

The passive implantable relay module may include a housing with an antenna lumen to enclose the first coupler arm, the connector portion, and the second coupler arm. The passive implantable relay module may include a housing with a stylet lumen to house a guiding device when the passive implantable relay module is being implanted.

In another aspect, some implementations provide a method of implanting a passive implantable relay module that includes implanting a passive implantable neural stimulator device inside a subject such that electrodes of the passive implantable neural stimulator device are positioned to deliver electric charges to excitable tissue; inserting a passive implantable relay module by snaking the passive implantable relay module through a tubing such that a distal coupler arm of the passive implantable relay module is placed substantially parallel to a receiving antenna on the passive implantable neural stimulator device; and placing a proximal coupler arm of the passive implantable relay module underneath the skin such that (i) the proximal coupler is configured to receive electromagnetic energy wirelessly and through non-inductive coupling from an external radio frequency pulse generator module placed outside the patient when the external radio frequency pulse generator module is activated, and (ii) the received electromagnetic energy is propagated along a connection portion of the passive implantable relay module to arrive at the distal coupler arm, which then wirelessly transmits the arrived electromagnetic energy, again through non-inductive coupling, to the receiving antenna on the passive wireless neural stimulator device.

Implementations may include one or more of the following features. Inserting the passive implantable relay module may include snaking the passive implantable relay module through the tubing on the passive implantable neural stimulator device.

BRIEF DESCRIPTION OF THE DRAWINGS

FIG. 4A shows a longitudinal view of an example of a relay module having two lumens.

FIG. 4B shows an axial view of an example of a relay module having two lumens.

FIG. 4C shows a schematic view of an example of a relay module.

FIG. 6B is a schematic view of an example of a relay module.

FIG. 6C is another schematic view of an example of a relay module.

Like reference symbols in the various drawings indicate like elements.

DETAILED DESCRIPTION

Figure 1:
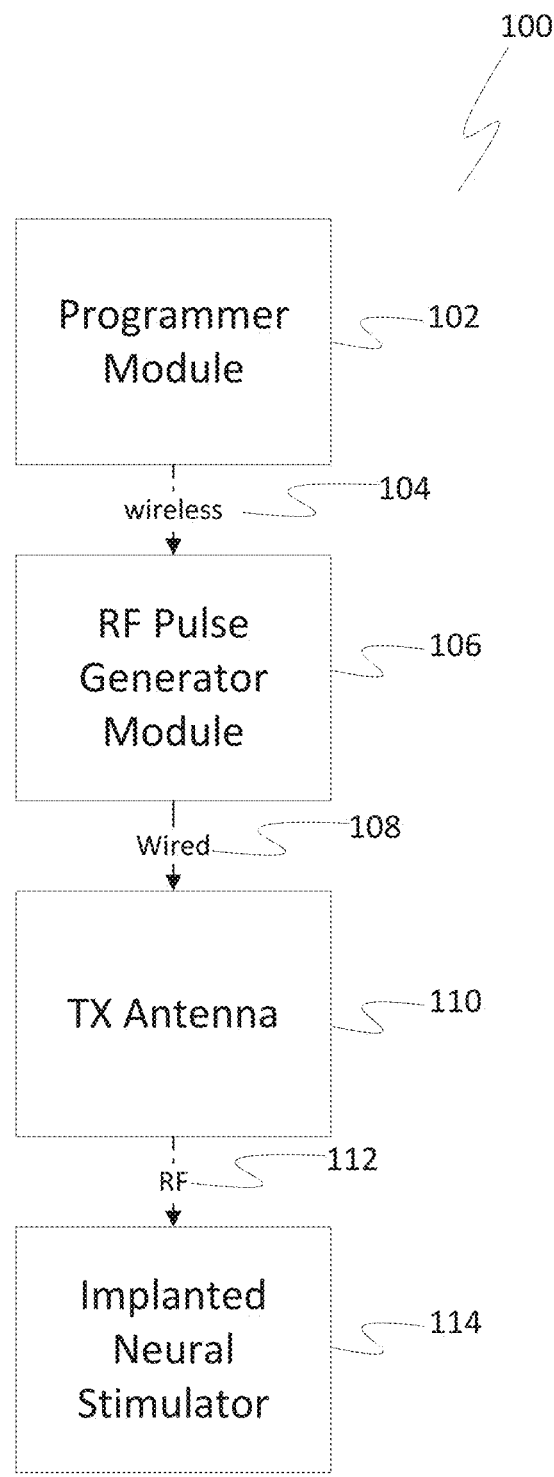
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power an implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling, and the received RF power is solely used to power the implantable stimulator device. This allows such devices to produce electrical currents capable of stimulating nerve bundles without a physical connection to an implantable pulse generator (IPG) or use of an inductive coil.

In some implementations, a passive relay module may be configured as an implantable device to couple electromagnetic energy radiated from an external transmitting antenna to a wireless implantable stimulator device. In one example, the implantable device includes two monopole coupler arms connected to each other by a coaxial (coax) cable. One monopole coupler arm may be implanted in a parallel configuration with the external transmitting antenna such that linearly polarized electromagnetic waves radiated from the external transmitting antenna are received by this monopole coupler arm. Through the coaxial cable, the received electromagnetic waves may propagate to the other monopole coupler arm. In a reciprocal manner, this monopole coupler arm may radiate the received electromagnetic energy to the receiving antenna of the stimulator device. To effectively radiate the received electromagnetic energy to the receiving antenna of the stimulator device, parallel alignment of this other monopole coupler arm and the receiving antenna again may be used. In some cases, lengths of the monopole arms and length the coax cable can be tailored to improve transmission efficiency, for example, at a particular operating frequency.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011, PCT/US2012/55746, filed Sep. 15, 2011, and PCT/US2015/030433, filed May 12, 2015, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmitting (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
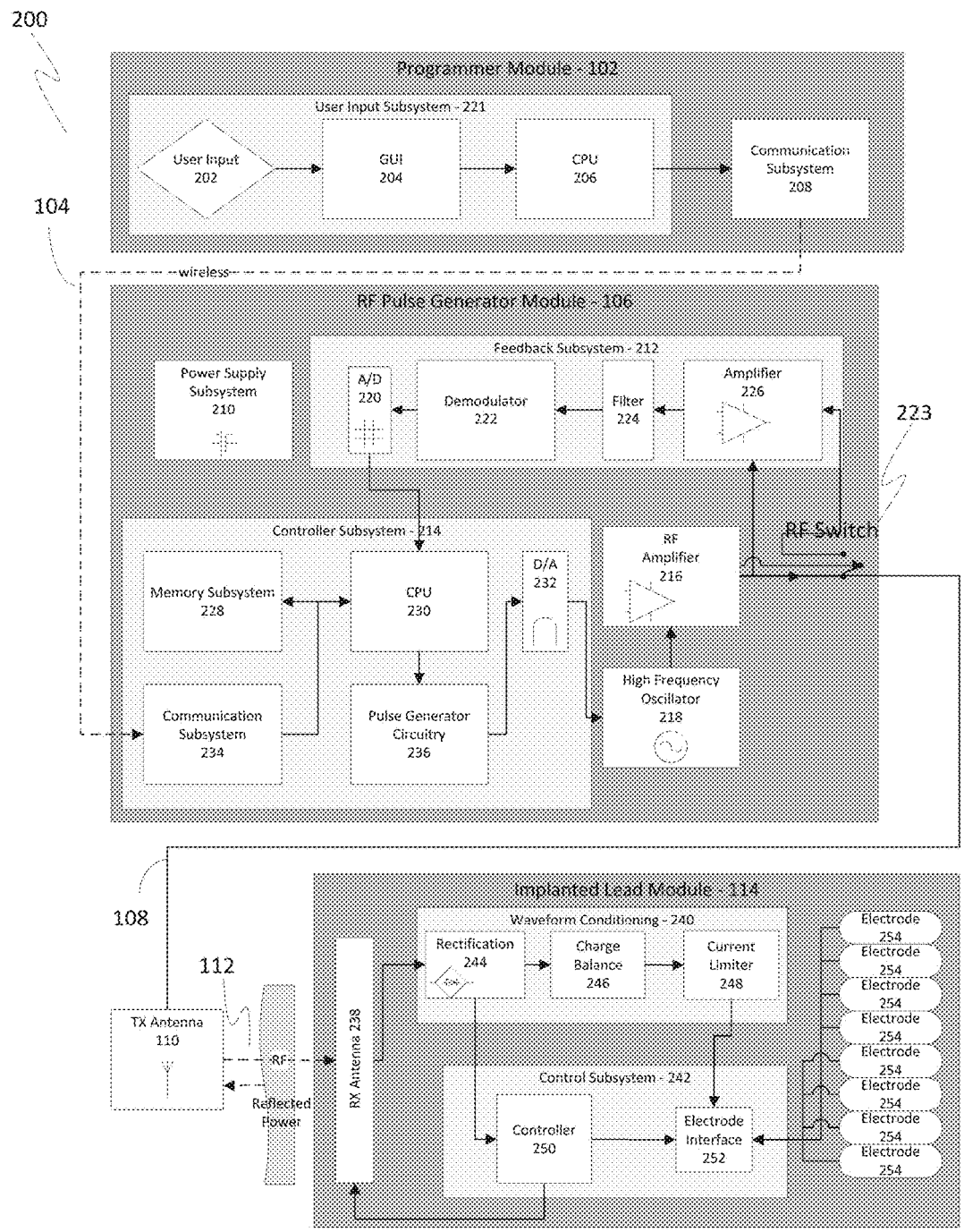
FIG. 2 depicts a more detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

Stimulation Parameter Table 1
Pulse Amplitude: 0 to 25 mA
Pulse Frequency: 0 to 20000 Hz
Pulse Width: 0 to 2 ms The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuro-anatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna (s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, the amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A delivered a stimulus phase, for example, 3 mA current for a duration of 200 microseconds followed by a 400 microseconds charge-balancing phase. This stimulus cycle, for example, could be specified to repeat at a rate of 60 cycles per second. Then, for set B, the controller 250 could specify a stimulus phase of 1 mA current for duration of 500 microseconds, followed by a 800 microseconds charge-balancing phase. The repetition rate for the set-B stimulus cycle can be set independently of set A, say for example, could be specified at 25 cycles per second. Or, if the controller 250 was configured to match the repetition rate for set B to that of set A, for such a case, the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm$^2$. In order to avoid the irreversible electrochemical reactions such as pH change, electrode dissolution as well as tissue destruction, no net charge should appear at the electrode-electrolyte interface, and it is generally acceptable to have a charge density less than 30 uC/cm$^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3A:
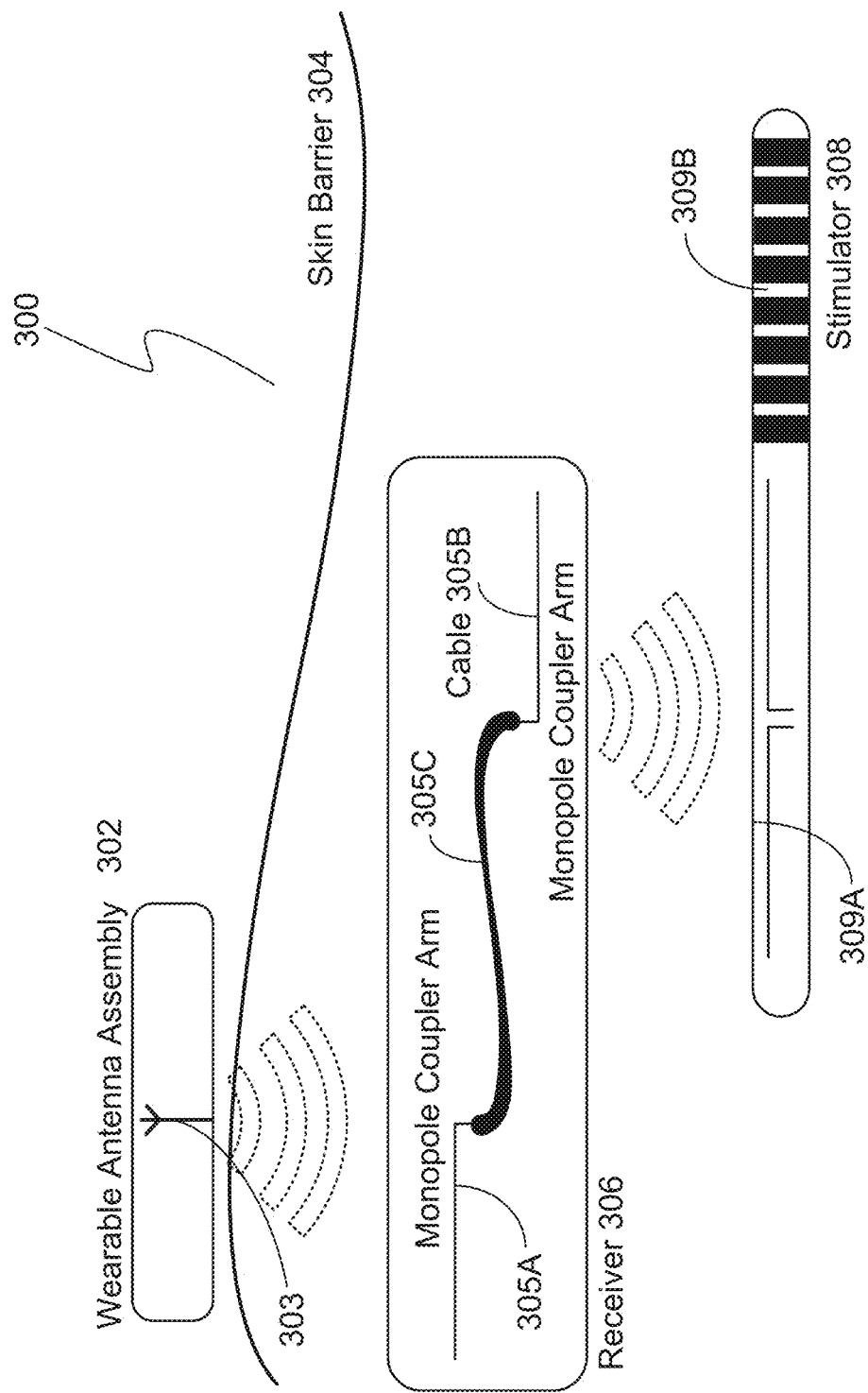
FIG. 3A is an illustration of an example of a relay module during operation.

FIG. 3A is an illustration 300 of an example of a relay module 306 during operation. A wearable antenna assembly 302 may be placed externally on a subject's skin. The wearable antenna assembly 302 may include a transmitting antenna 303 as a specific implementation of transmitting antenna 110. The transmitting antenna 303 may transmit an input signal containing electric energy and stimulation pulse parameters through electric radiative coupling and not inductive coupling to relay module 306.

To improve transfer efficiency of electromagnetic energy into the body, it may be advantageous to make use of an implanted intermediate device, such as relay module 306, that receives energy from the transmitter just under the skin then transports the energy deeper into the body where it can be released to the implanted stimulator receiver circuitry, for example, implantable stimulator device 308 to reduce loss of RF energy due to absorption in the body tissue. Relay module 306 may also be referred to as a receiver device.

Relay module 306 may include a first monopole coupler arm 305A, a second monopole coupler arm 305B, and a coax cable portion 305C connecting the first and second monopole coupler arms 305A and 305B. As illustrated, monopole coupler arm 305A receives electromagnetic energy radiated from transmitting antenna 303. Monopole coupler arm 305A and the transmitting antenna 303 are generally aligned in parallel along their longitudinal axes. In some instances, transmitting antenna 303 may launch a linearly polarized electromagnetic wave in which the direction of this linear polarization is in general alignment with the longitudinal axis of monopole arm 305A. In one instance, the transmitting antenna 303 may be configured as a dipole antenna whose longitudinal direction is aligned with that of monopole coupler arm 305A. In another instance, the transmitting antenna 303 may be configured as a patch antenna configured to transmit electromagnetic energy that is linearly polarization along the longitudinal direction of monopole coupler arm 305A. In these instances, monopole arm 305A may be placed at a shallow depth, for example, just under the skin, such that it couples, through the electric radiative coupling, to transmitting antenna 303 just outside the skin 304. Through cable 305C, the received electromagnetic energy may travel to the other monopole arm 305B. Cable 305C can be a coaxial cable with an outer shield that encloses dielectric material, which in turn surrounds a metal core. Cable 305C can also be implemented as a wire that includes the metal core and the surrounding dielectric but not the outer shield. Cable 305C between the two monopole coupler arms 305A and 305B may guide the received electromagnetic RF energy from monopole coupler arm 305A to monopole arm 305B while shielding the received electromagnetic RF energy from body tissue such that energy losses during propagation is reduced. Notably, monopole coupler arm 305B may be placed deeper in the tissue while maintaining close proximity to the implanted stimulator device 308 so that such that it couples to the receiving antenna 309A of the implantable neural stimulator device 308. Monopole coupler arm 305B may transmit the electromagnetic energy using linearly polarized waves and through electric radiative coupling to the receiving antenna 309A of the implantable neural stimulator device 308. Monopole coupler arm 305B may be generally aligned with receiving antenna 309A such that the electromagnetic waves launched from monopole coupler arm 305 are linearly polarized along the direction of the receiving antenna 309A (e.g., a dipole antenna).

Figure 3B:
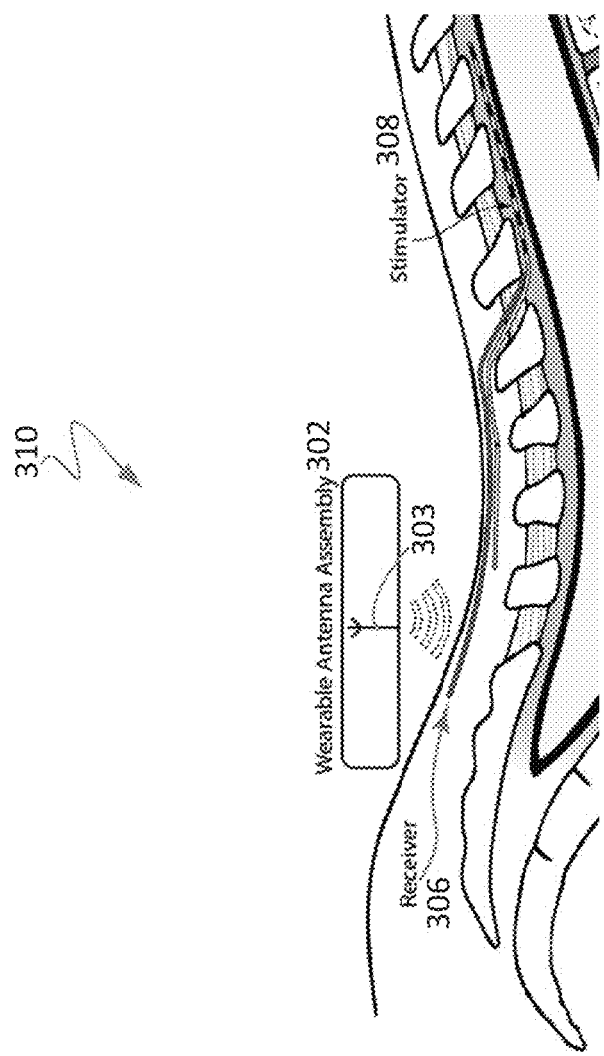
FIG. 3B is another illustration of an example of a relay module during operation.
Figure 3C:
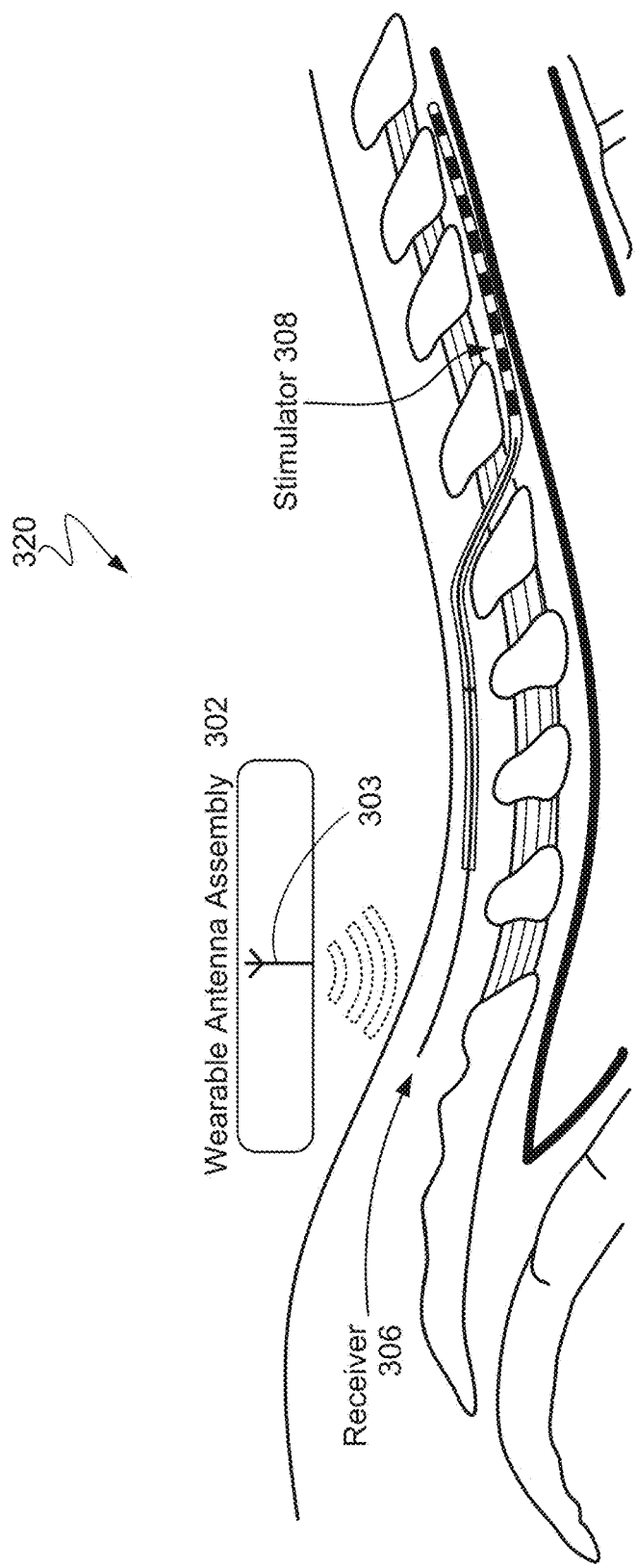
FIG. 3C is yet another illustration of an example of a relay module during operation.

While monopole arms 305A and 305B are generally aligned with transmitting antenna 303 and receiving antenna 309A, cable 305C may not be subject to such placement restrictions. Indeed, in some instances, cable 305C may be configured to include a bend, a turn, or even a twist. Referring to FIGS. 3B-3C, respective examples 310 and 320, each shows a relay module 306 to bridge electromagnetic energy transmission from wearable antenna assembly 302 to implantable neural stimulator device 308 that has been implanted in the intervertebral space for spinal cord treatment. In FIG. 3B, cable 305C of the relay module 306 (also known as the receiver device) is inserted into an inner tubing of a passive wireless stimulator device 308 so that coupler arm 305B comes into alignment proximity with the receiving antenna of the implantable neural stimulator device 308, however it remains separated by the inner lumen wall of the implantable neural stimulator device 308. As illustrated in FIG. 3C, the cable 305C of the relay module 306 (also known as the receiver device) may wind its way through the intervertebral space and the path can include non-straight segments, such as turns and bends so that coupler arm 305B comes into alignment proximity of receiving antenna of the implantable neural stimulator device 308. In another example, the cable may be outside of the lumen of the implantable neural stimulator device 308, separately placed, but in alignment proximity to the implantable neural stimulator device 308.

Referring to FIGS. 4A-4B, an example of a relay module 400 is shown. Relay module 400 may be configured as a flexible enclosure or housing made from a biocompatible material. Relay module 400 may include heat sealed tips 402A and 402B that are round to be seated in tissue without irritation. As illustrated, the rounded corners can have a radius of 1.35 mm. In some instances, heat sealed tips 402A and 402B may include suture sites to allow relay module 400 to be secured to surrounding tissue at implantation. In some instances, relay module 400 may have markers (e.g., in the form of barbs or anchors) that can stop relay module 400 from moving/displacing after the relay module 400 has been implanted. Relay module 400 may include module body 402C that houses a stylet lumen 404 and an antenna lumen 406. Stylet lumen 404 may have a diameter of 0.55 mm to house a fine-size stylet (e.g., at gauge 25). A stylet or a guidewire may be placed, through stylet entry 404A, inside the stylet lumen 404 to navigate the placement of relay module 400. Once the relay module 400 has been placed at a desirable location inside the subject, the guidewire or stylet may be withdrawn from the stylet lumen 404 through stylet entry 404A. Antenna lumen 406, on the other hand, may be closed and without entries to enclose relay module 306. FIG. 4C shows a schematic view of an example of a relay module 306. As depicted in this example, relay module 306 includes monopole coupler arms 305A and 305B as antenna signal probes, each with a length of 20 mm. In this example, the relay module 306 also includes shielded coax cable 305C with a length of 60 mm and a diameter of 0.5 mm to fit inside antenna lumen 406.

Figure 5A:
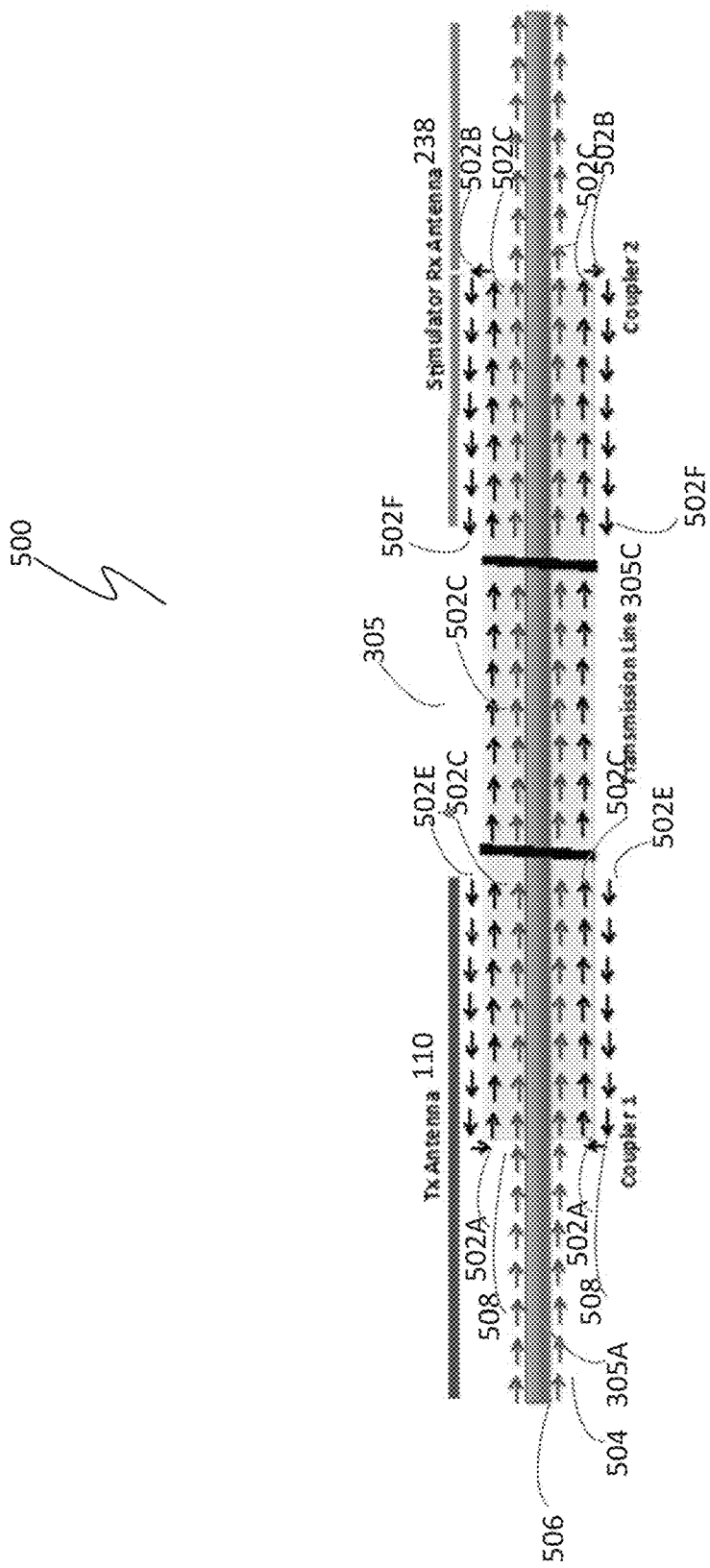
FIG. 5A illustrates current flow in an example of a relay module when the relay module receives radiated electromagnetic energy from an external transmitting antenna and then channels the energy to the receiving antenna on a stimulator.

FIG. 5A is a diagram 500 of a relay module 306 bridging electromagnetic energy transmitted from an external TX antenna 110 to receiving antenna 238. In this example, RF energy is transmitted from TX antenna 110 into the body. The electric radiative coupling between the TX antenna 110 and monopole coupler arm 305A can cause a surface current 502E on the exterior of the shield of coax cable 305C as well as a surface current 504 on the center conductor that runs from monopole coupler arm 305A to monopole coupler arm 305B. In this illustration, the current 504 on the center conductor continues along the length of the center conductor. The surface current 502E, on the other hand, flows on the exterior of the shield, wraps around a corner 508 of the outer coax shield as current 502A, proceeds as current 502C on the inside of the outer coax shield, wraps around the other corner 510 of the outer coax shield as current 504B, and then flows on the exterior of the coax shield as current 502F. While surface current 502E and surface current 502F do exist and travel on the outside of the coax cable 305C, such surface currents are exposed to body tissue. As a result, the flux of such surface current will decay exponentially by approximately half its value, for example per every centimeter (at an operating frequency of 915 MHz) of travel along the exterior of coax cable 305C. Hence, electrical energy that can reach from one monopole coupler arm to the other monopole coupler arm via the outside of the coax may decay rapidly with increasing length. The electromagnetic field that arises due to current 502C will couple to and drive the Rx antenna 238 on the wireless passive neural stimulator 114. Indeed, once electromagnetic energy is coupled to monopole arm 305A and current 504 is generated on center conductor, this electromagnetic energy is transported down the length of the coax cable 305C, with negligible losses, to the monopole coupler arm 305B so that the electromagnetic energy is radiated to Rx antenna 238 on implanted neural stimulator 114. Generally, density of current 504 approaches zero at the two ends of the center conductor while the density of current 504 may reach a maxima on the center conductor at the locations corresponding to two ends of the outer conductor, namely corner 508 and corner 510. When in resonance, the density distribution of current 504 on the center conductor may approach a half wave sinusoid between end 506 and the location at the level of corner 508 on the center conductor (the peak) as well as between end 512 and the location at the level of corner 510 on the center conductor (the peak).

As explained in further detail below, a variety of coax cable configurations may be used, including a 42 AWG coax, and up to 32 AWG coax (U. Fl.) configuration. The length for the coupler arm's exposed center conductor may be beneficially set around 5 cm. This length applies to each of the two-coupler arm, but can be adjusted to a range of sizes.

Table 1 documents an example of measuring voltage on the relay module when transmitting electromagnetic energy through a 5 mm thick layer of neoprene to a 42 AWG receiver that includes a coax cable.

TABLE 1

Measurements taken in air, with the coupler placed in the lumen of the stylet.

| MFS Index | Antenna Input Power (Watts) | Voltage Full Bridge | Voltage Half Bridge | Voltage Ratio (Full/Half) |
|---|---|---|---|---|
| 0 | 0.08 | 0.80 | 0.34 | 2.35 |
| 1 | 0.10 | 0.96 | 0.39 | 2.46 |
| 2 | 0.13 | 0.93 | 0.45 | 2.07 |
| 3 | 0.17 | 1.20 | 0.53 | 2.26 |
| 4 | 0.21 | 1.30 | 0.60 | 2.17 |
| 5 | 0.26 | 1.41 | 0.69 | 2.04 |
| 10 | 0.75 | 2.36 | 1.26 | 1.87 |

The estimated stimulator output (including voltage and current) based on power scaling resulting from power measurements of Table 1 is shown in Table 2.

TABLE 2

Estimated Stimulator output, with the coupler placed in the lumen.

| Index | Power (Watts) | Power Scale | Scaled Stimulator Voltage (V) | Scaled Stimulator Current (mA) |
|---|---|---|---|---|
| 0 | 0.08 | 1.00 | 0.80 | 1.60 |
| 1 | 0.10 | 1.28 | 0.91 | 1.81 |
| 2 | 0.13 | 1.64 | 1.03 | 2.05 |
| 3 | 0.17 | 2.12 | 1.17 | 2.33 |
| 4 | 0.21 | 2.66 | 1.30 | 2.61 |
| 5 | 0.26 | 3.37 | 1.47 | 2.94 |
| 6 | 0.33 | 4.23 | 1.64 | 3.29 |
| 7 | 0.42 | 5.30 | 1.84 | 3.68 |
| 8 | 0.50 | 6.41 | 2.03 | 4.05 |
| 9 | 0.62 | 7.89 | 2.25 | 4.49 |
| 10 | 0.75 | 9.59 | 2.48 | 4.96 |
| 11 | 0.92 | 11.67 | 2.73 | 5.47 |
| 12 | 1.12 | 14.22 | 3.02 | 6.03 |
| 13 | 1.58 | 20.18 | 3.59 | 7.19 |
| 14 | 1.59 | 20.28 | 3.60 | 7.20 |
| 15 | 1.91 | 24.27 | 3.94 | 7.88 |
| 16 | 2.26 | 28.77 | 4.29 | 8.58 |
| 17 | 3.02 | 38.46 | 4.96 | 9.92 |
| 18 | 3.69 | 46.99 | 5.48 | 10.97 |
| 19 | 4.47 | 56.89 | 6.03 | 12.07 |
| 20 | 5.30 | 67.45 | 6.57 | 13.14 |
| 21 | 7.00 | 89.13 | 7.55 | 15.10 |
| 22 | 8.97 | 114.29 | 8.55 | 17.10 |
| 23 | 11.07 | 140.93 | 9.50 | 18.99 |

In another experiment, coupling the relay module through 1 cm of phantom solution to a transmitting antenna yielded 2.8 mA on stimulator device for index 23 (~11 Watts). From this point on, increasing the power by a scale of 3 can yield 10 mA on stimulator device (not tabulated in Table 2).

Figure 5B:
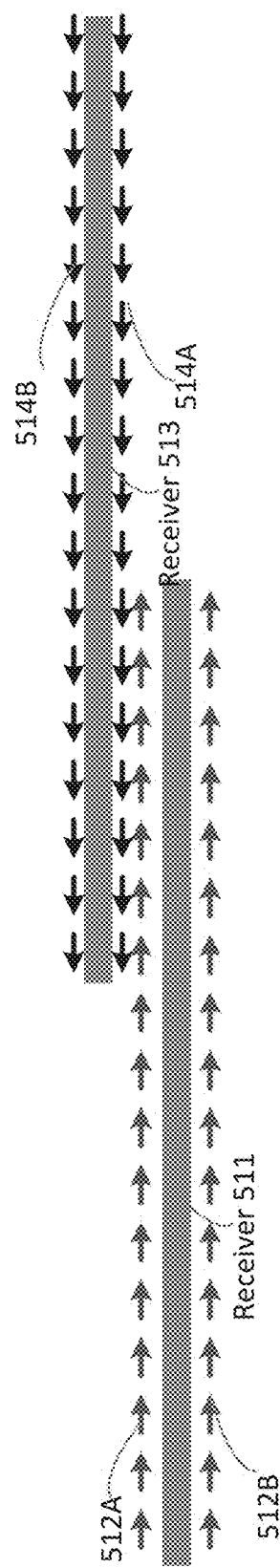
FIG. 5B illustrates electric charge flow in an example of a relay module that includes two partially overlapping connector portions of metal core.

To mitigate the safety concern of heating, the relay module may include two or more conducting wires with overlapping sections. The conducting wires do not come into electrical contact as they are insulated. FIG. 5B illustrates one example of two conducting wires that overlap. The overlap allows filtering of the electric fields that result from potential charge build-up. In more detail, in a longer wire, the charge build-up due to oscillating MRI fields can lead to currents that flow from one end to the other. The overlap configuration, as illustrated FIG. 6, establishes a current path on two independent conductors so that the current caused by oscillating MRI fields cannot flow freely along the total length of the combined conducting wires. At the same time, however, the overlapping configuration of using more than one wire does not pose a major barrier at the transmitting frequency of the external RF pulse generator. This is because this transmitting frequency is typically much higher than the operating frequency of the MRI. In particular, while an overlap of 10 cm may be a half-wavelength for the transmitting frequency, this gap of 10 cm would be far under the half-wavelength for the operating frequency of the MRI. As such, this gap configured as an overlapping arrangement can achieve filtering to effectively mitigate the deleterious effects of the SAR issue for MRI. As illustrated in FIG. 5B, currents 512A and 512B from the monopole couple arm (due to electromagnetic energy received non-inductively from an external antenna assembly—such as a wearable antenna assembly) on receiver 511 can cause currents 514A and 514B on relay module 513. The arrows in FIG. 5B indicate the sign of the charge and direction of charge flow along the overlap section of the relay at the transmitter frequency, resulting in a net current flow along the length of the relay. Relay module 513 can further transfer the electromagnetic energy to a passive implantable stimulator device.

Figure 6A:
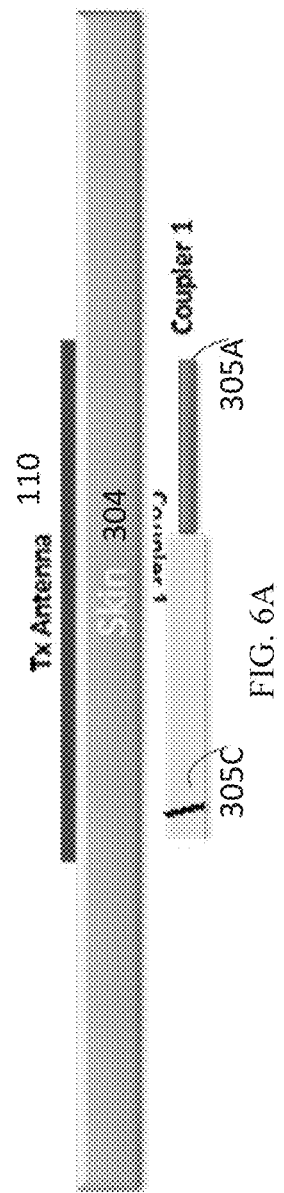
FIG. 6A is a schematic view of an example of using a relay module to receive electromagnetic energy from an external transmitting antenna.
Figure 6D:
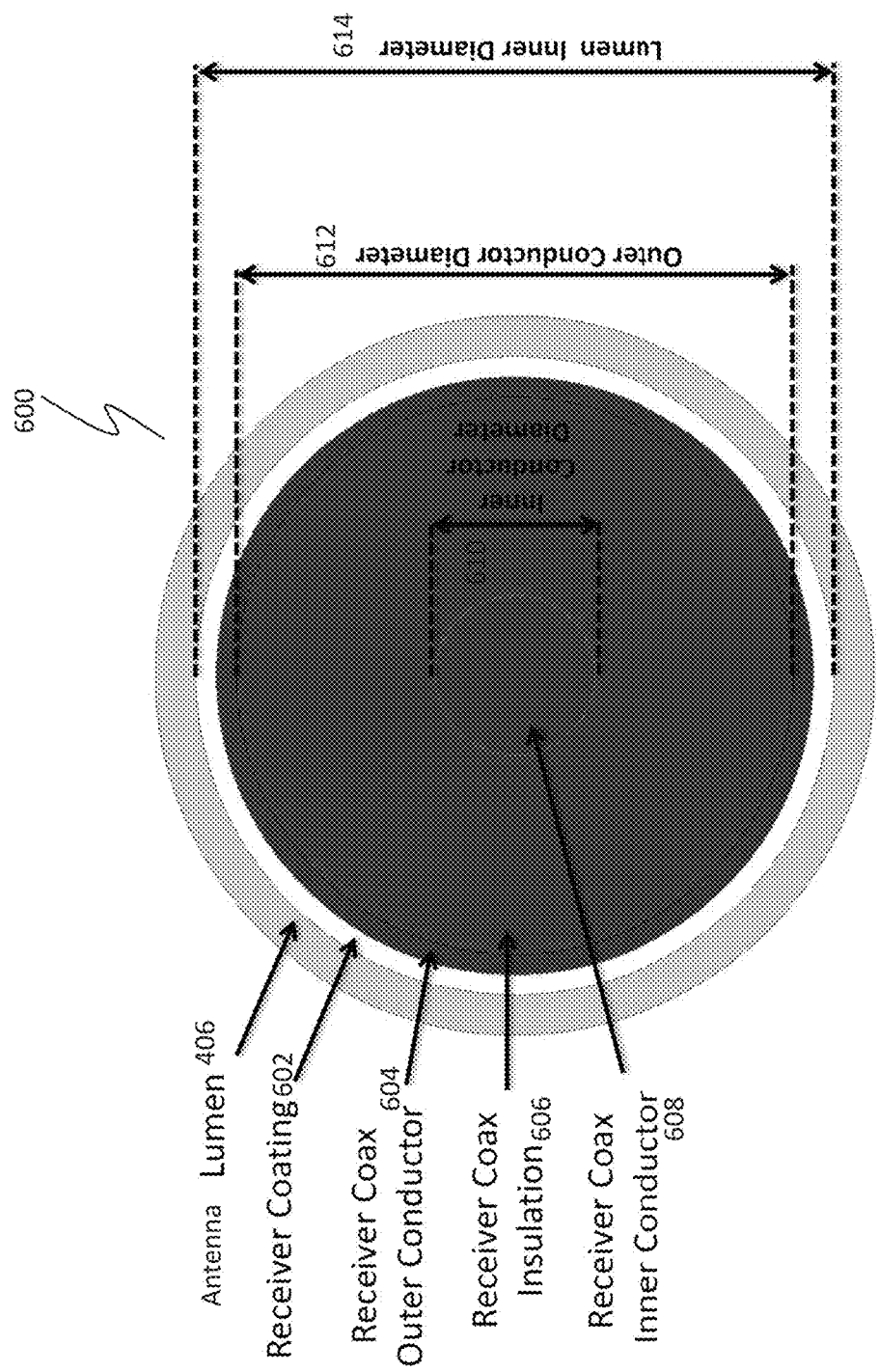
FIG. 6D is an axial view of a coax section of an example of a relay module.
Figure 6E:
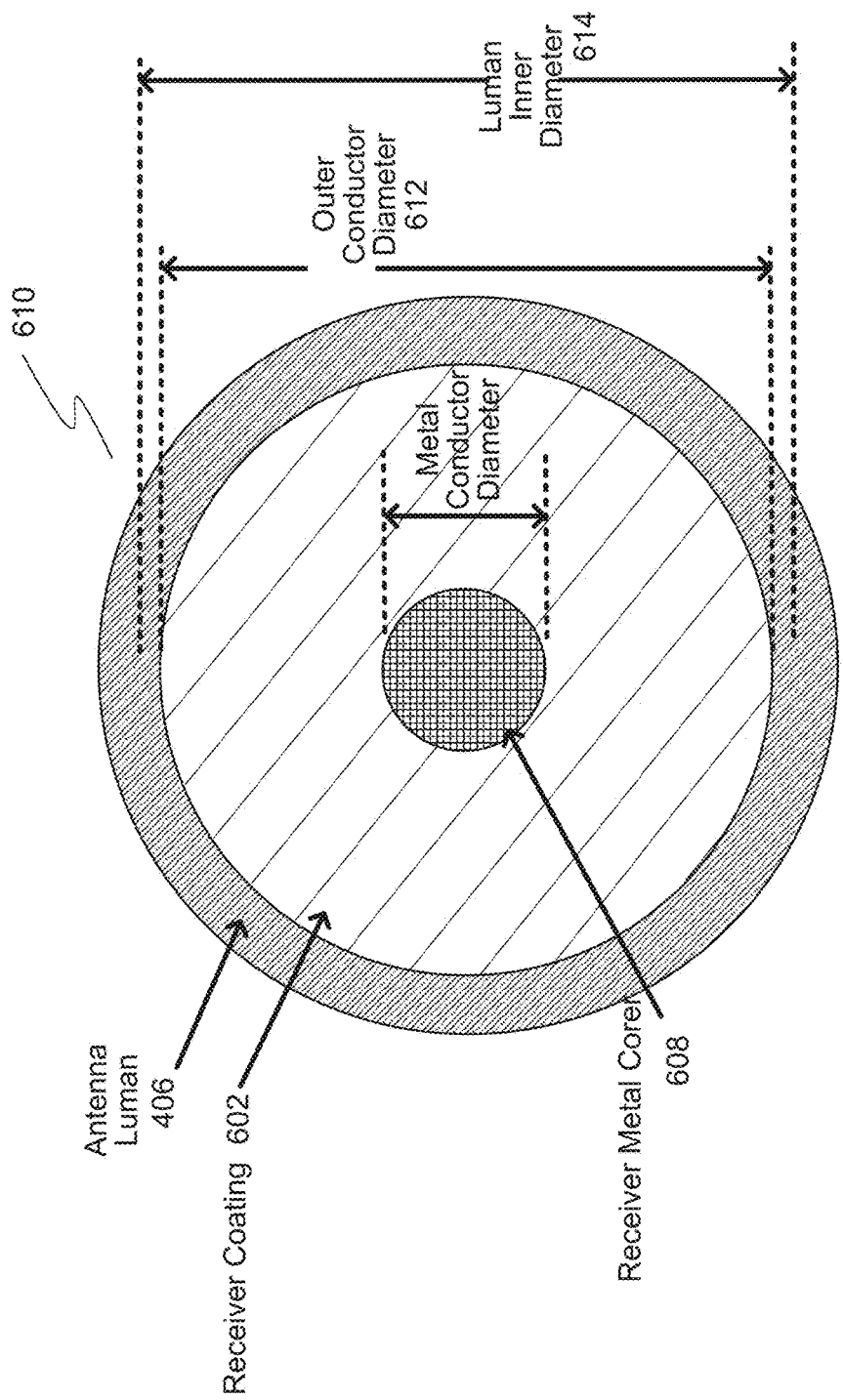
FIG. 6E is an axial view of a wire section of an example of a relay module.

Referring to FIGS. 6A to 6F, an example of a relay module is illustrated to couple electromagnetic energy from transmitting antenna 110 through skin 304 to monopole coupler arm 305A. In these examples, monopole coupler arm 305A and monopole coupler arm 305B of relay module 306 are connected by cable 305C that is modeled as a transmission line (for the purpose of simulation investigations). In these examples, cable 305C can be configured as a coaxial implementation with an outer shell, or a wire configuration that is without the outer shell. In more detail, FIGS. 6D and 6E show the cross-sectional views at location B-B respectively for the coaxial implementation (FIG. 6D) and wire implementation (FIG. 6E).

In more detail, FIG. 6D shows an axial view of, for example, a coax section of relay module 306 located in antenna lumen 406 with a lumen inner diameter of 614. Relay module 306 may also be known as a receiver and may include receiver coating 602 as the outer cover to enclose receiver coax outer conductor 604, receiver insulation 606, and receiver coax inner conductor 608. Receiver coax outer conductor 604 may have an outer conductor diameter 612. Receiver coax inner conductor may have an inner conductor diameter 610. In this example, receiver insulation 606 fills the space between the inside of outer conductor 604 and outside of inner conductor 608.

FIG. 6E shows an axial view of a wire section of an example of a relay module 306 located in antenna lumen 406 with a lumen inner diameter of 614. Relay module 306 may also be known as a receiver and may include receiver coating 602 as the outer cover to enclose receiver insulation 606, and receiver conductor 608. Receiver conducting conductor may have a conductor diameter 610. In this example, receiver insulation 606 surrounds receiver conductor 608.

In some implementations, the metal core may include gold-plated stainless steel. Other metals may also be used, for example, copper, aluminum, or alloys. In one example, to increase rigidity of the relay module that may fit into the lumen of the stimulator device (or lead), gold platted stainless steel can be used. The coating may include low loss dielectric, for example, implantable, high-strength, and high performance polymer, PolyEtherEtherKetone (PEEK).

The length of a relay module for relaying energy from the body surface to the receiving antenna of the stimulator may be about 20 cm, depending on the implant scenario. The length may be longer, or shorter. In those cases where there may not be an ideal resonance, longer Receiver lengths may be sufficient to transmit energy to the Stimulator by adjusting other factors such as the Tx antenna RF power level. The placement of the distal end of the Receiver conductor must be such that the maximum electric field interacts with the Rx antenna. That is the distal end of the Receiver conductor must terminate near the distal end of the Stimulator Rx antenna.

Figure 6F:
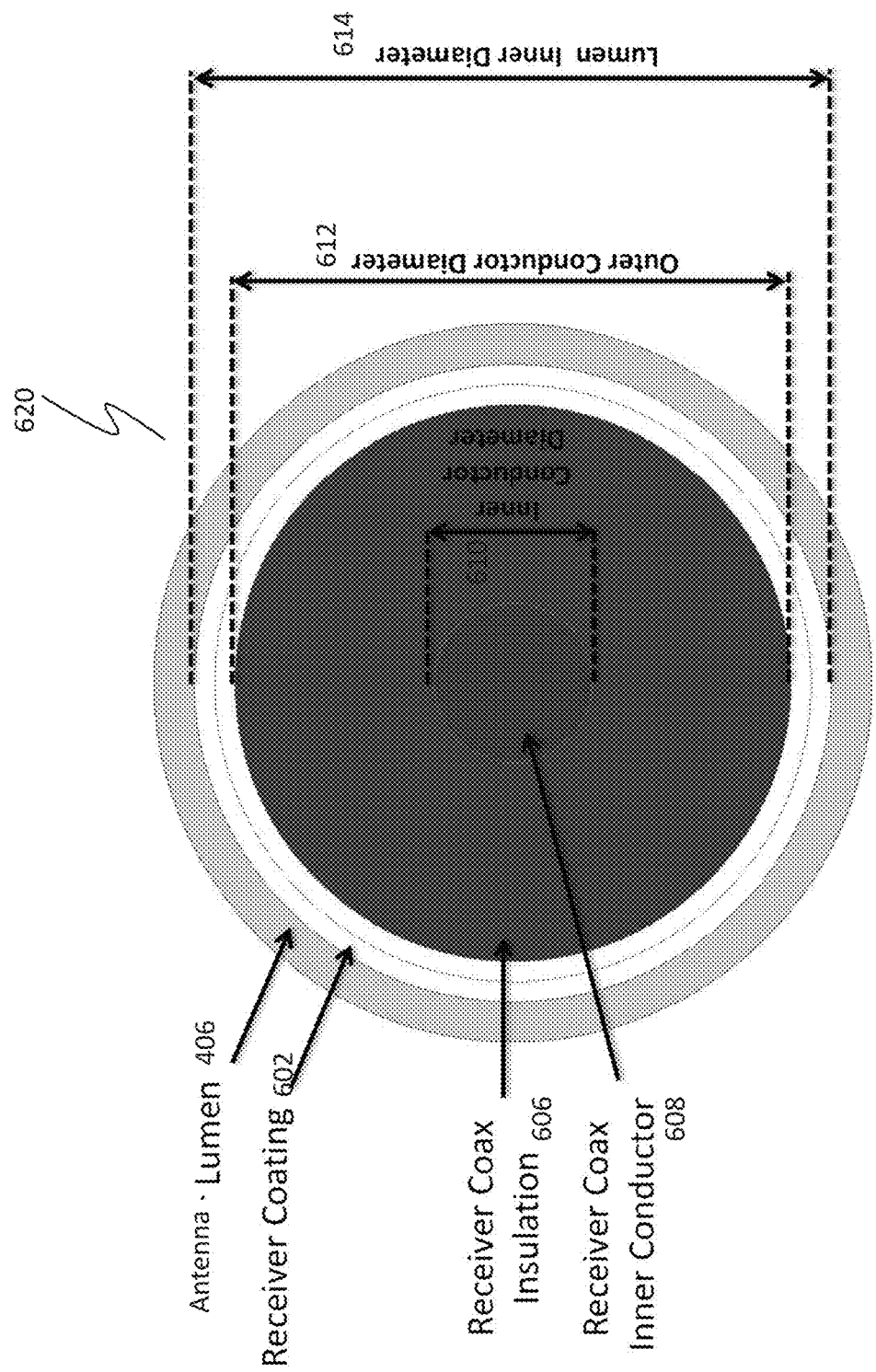
FIG. 6F is an axial view of a coupler end of an example of a relay module.

FIG. 6F shows an axial view of a coupler end (location A-A in FIG. 6B) of an example of a relay module 306 located in antenna lumen 406 with a lumen inner diameter of 614. In this illustration, receiver coating 602 is the outer cover that encloses receiver insulation 606, and receiver coax inner conductor 608. Receiver coax inner conductor may have an inner conductor diameter 610. Receiver insulation 606 may wrap around the outside of inner conductor 608.

These illustrated examples may include stopper 305D at the distal end of coupler arm 305B. Stopper 305D can cause the distal end of the examples of relay module to stop once a desired placement of the relay module is reached with respect to the receiving antenna on the passive implantable stimulator device.

As demonstrated in FIGS. 7 through 9, the presence of the relay module 306 inside a patient may not significantly impact the propagation of electromagnetic waves inside the body. FIGS. 10 through 11 show simulations that demonstrate the dependency of transmission efficiency on a variety of parameters.

Figure 7A:
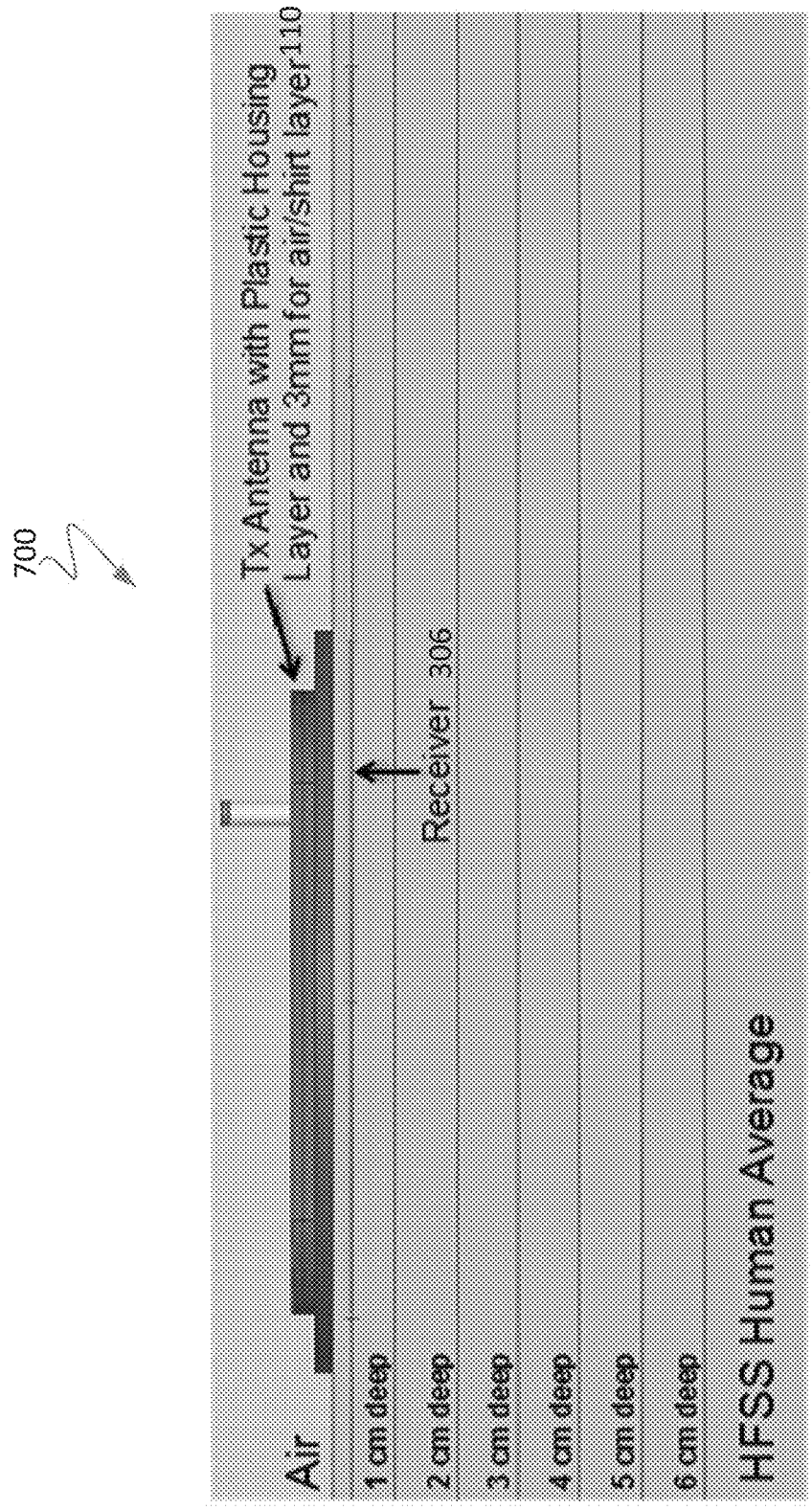
FIG. 7A illustrates an external transmitting antenna coupling to an example of a relay module that is implanted inside a subject and underneath the skin.

In particular, FIG. 7A illustrates an external transmitting antenna 118 coupling to an example of a relay module 306 that is implanted inside a subject and underneath the skin. In this simulation 700, transmitting antenna 118 is modeled to include a plastic housing layer as well as a 3 mm separation from skin to account for air/shirt space that is expected during operation. Additionally, in this example, the relay module 306 is placed approximately 3 mm underneath the skin.

Figure 7B:
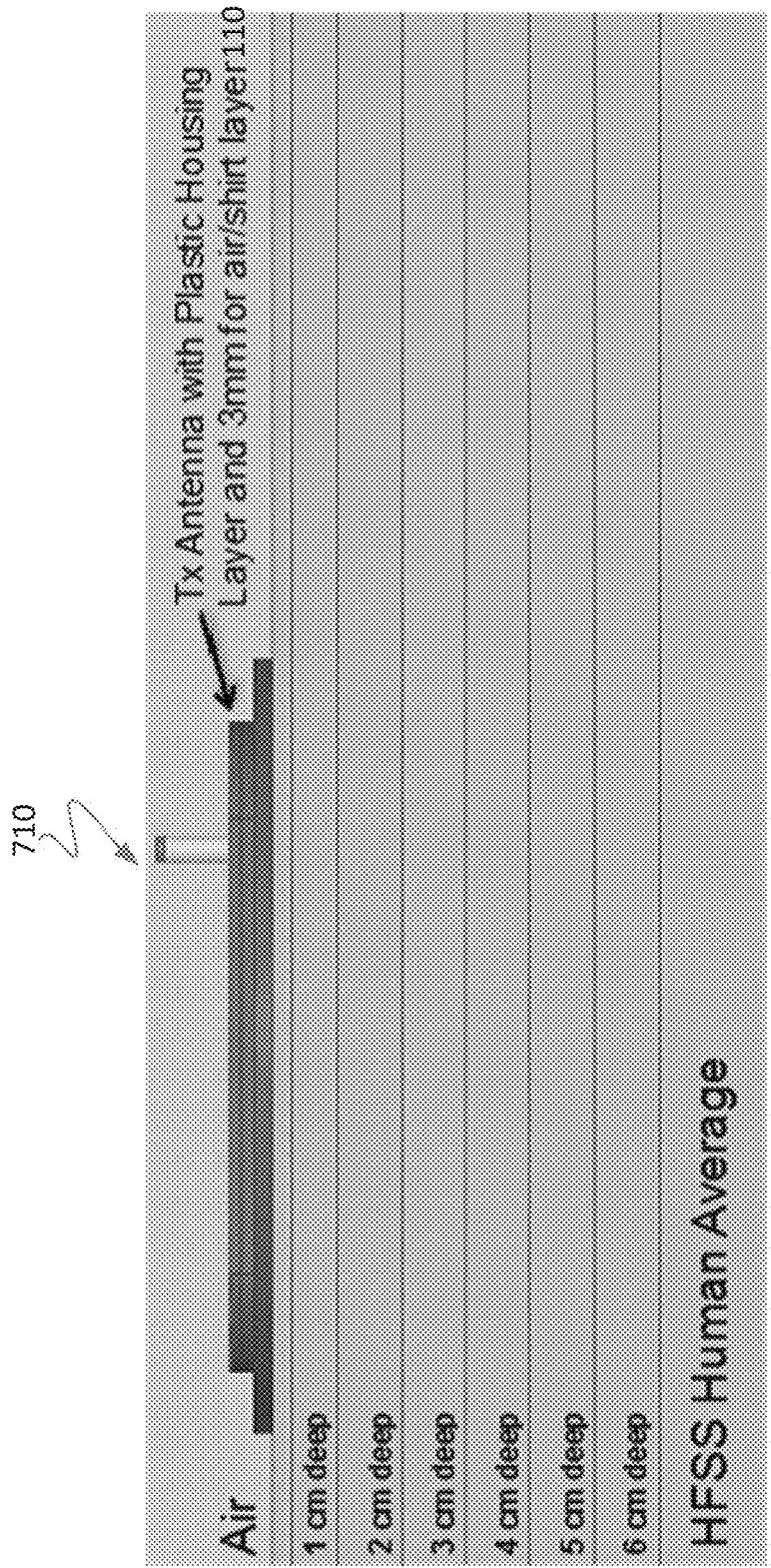
FIG. 7B illustrates an external transmitting antenna transmitting electromagnetic energy towards the inside of the subject when the implantable relay module has not been implanted.

In comparison, FIG. 7B illustrates an external transmitting antenna 118 transmitting electromagnetic energy towards the inside of the subject when the implantable relay module has not been implanted. In this simulation 710, transmitting antenna 110 is modeled to include a plastic housing layer as well as a 3 mm separation from skin to account for air/shirt encountered during transmission. Neither relay module 306 nor implantable stimulator device 308 are present.

In these simulations, transmitting antenna 110 has an average input power of 450 mW. The port impedance of the antenna is modeled as a 500 ohm load. The relay module 306 may have outer conductor diameter and inner conductor diameter of approximately 0.5 mm and 2 mm, respectively. The total length of the simulated relay module 306 is 20 cm while the length of the exposed center conductor at each end is 5 cm. Receiving antenna model is 0.75 mm in diameter and 9 cm long. The simulation also models relay module 306 and receiving antenna 238 of neural stimulator 114 as in alignment with each other. The dielectric insulation for the receiving antenna 238 is air-based. The dielectric of the coax cable 305 has a relative permittivity of 2.

Generally, the highest contribution of SAR in the presence of the relay module 306 is expected to be at the end of the coax outer conductors of relay module 306. This expected outcome may stem from the current dipole developed at the ends giving rise to incident field interaction. The highest field intensity is expected to occur at resonance. An increase in input power to the TX antenna 110 will lead to an increase in the field strength. Generally, the closer the relay module 307 is placed relative to the transmitting antenna 110, the stronger this field is expected to be.

Figures 8A, 8B:
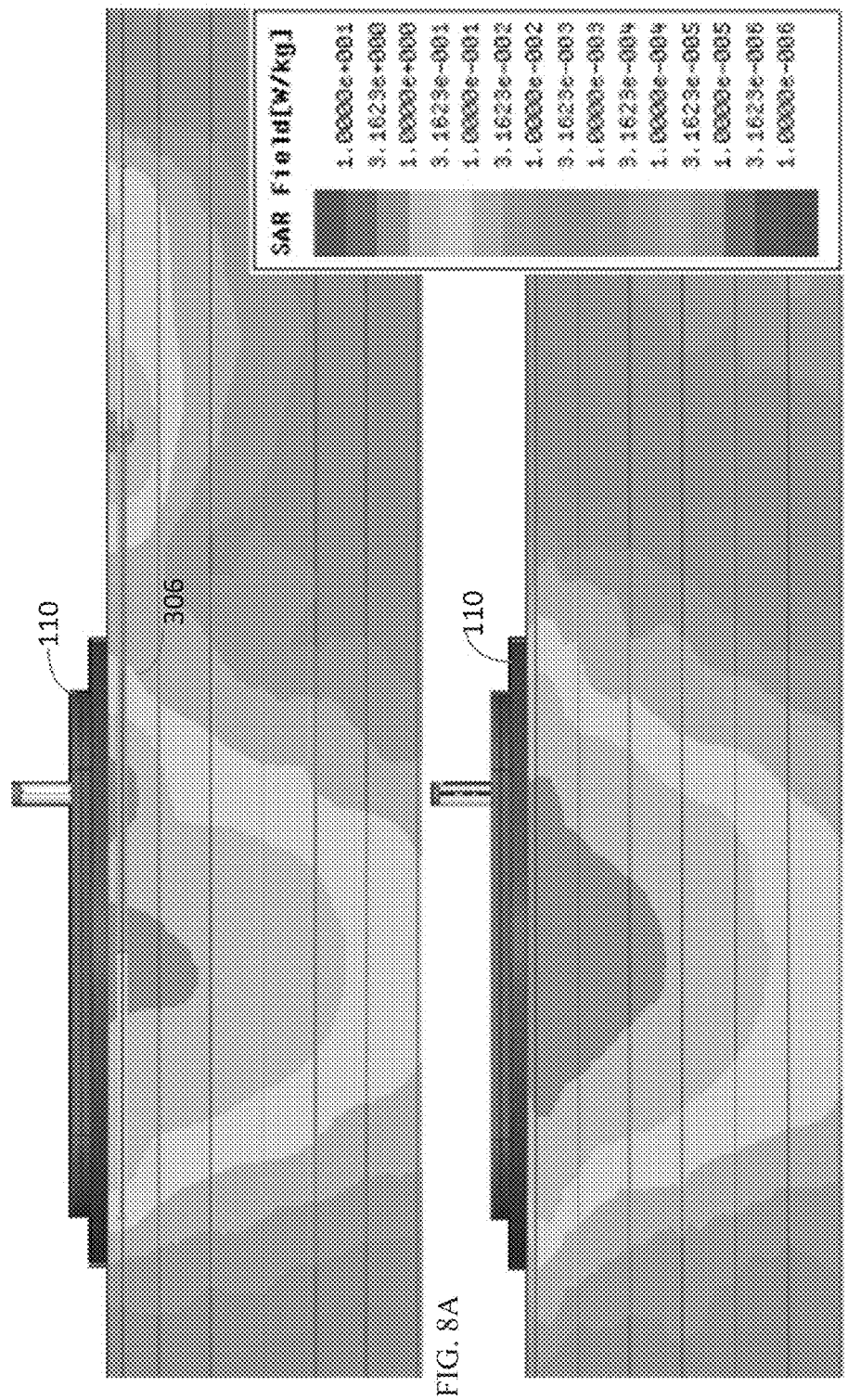
FIG. 8A shows an in-depth view of the simulated SAR pattern from the simulation illustrated in FIG. 7A.
FIG. 8B shows an in-depth view of the simulated SAR pattern from the simulation illustrated in FIG. 7B.
Figure 9A:
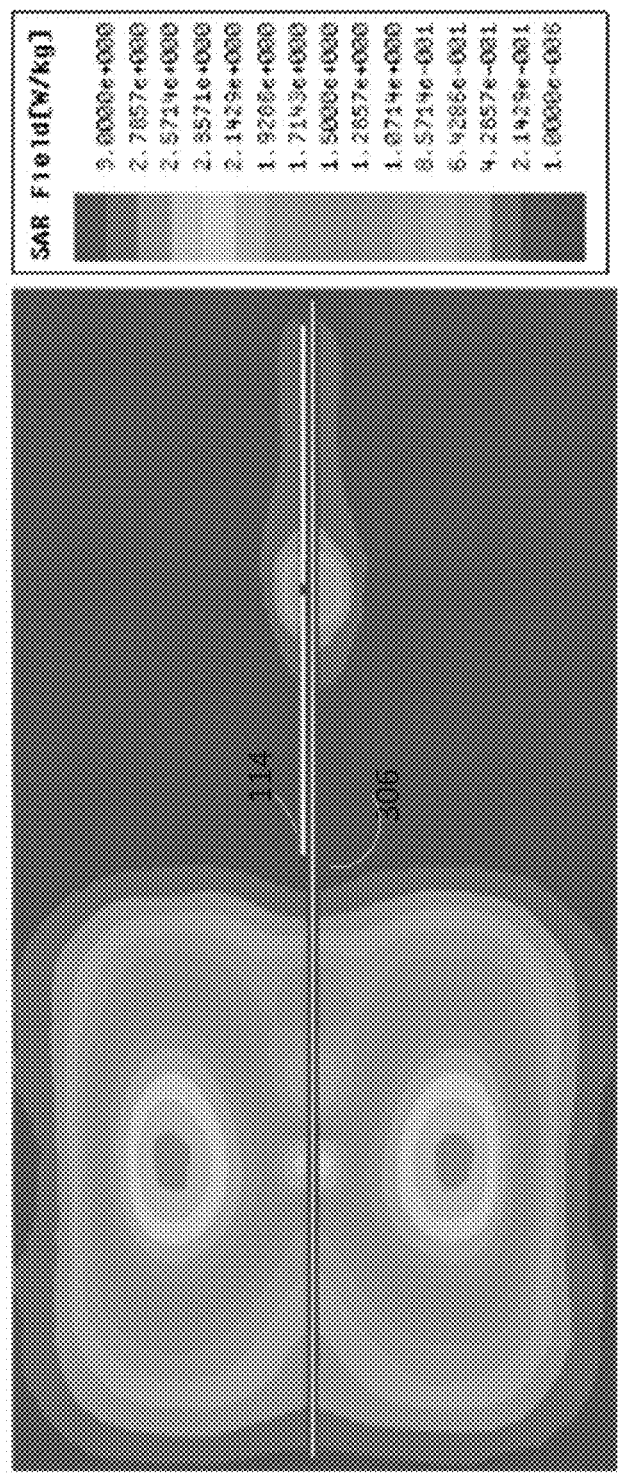
FIG. 9A shows a planar view of the simulated SAR pattern from the simulation illustrated in FIG. 7A.
Figure 9B:
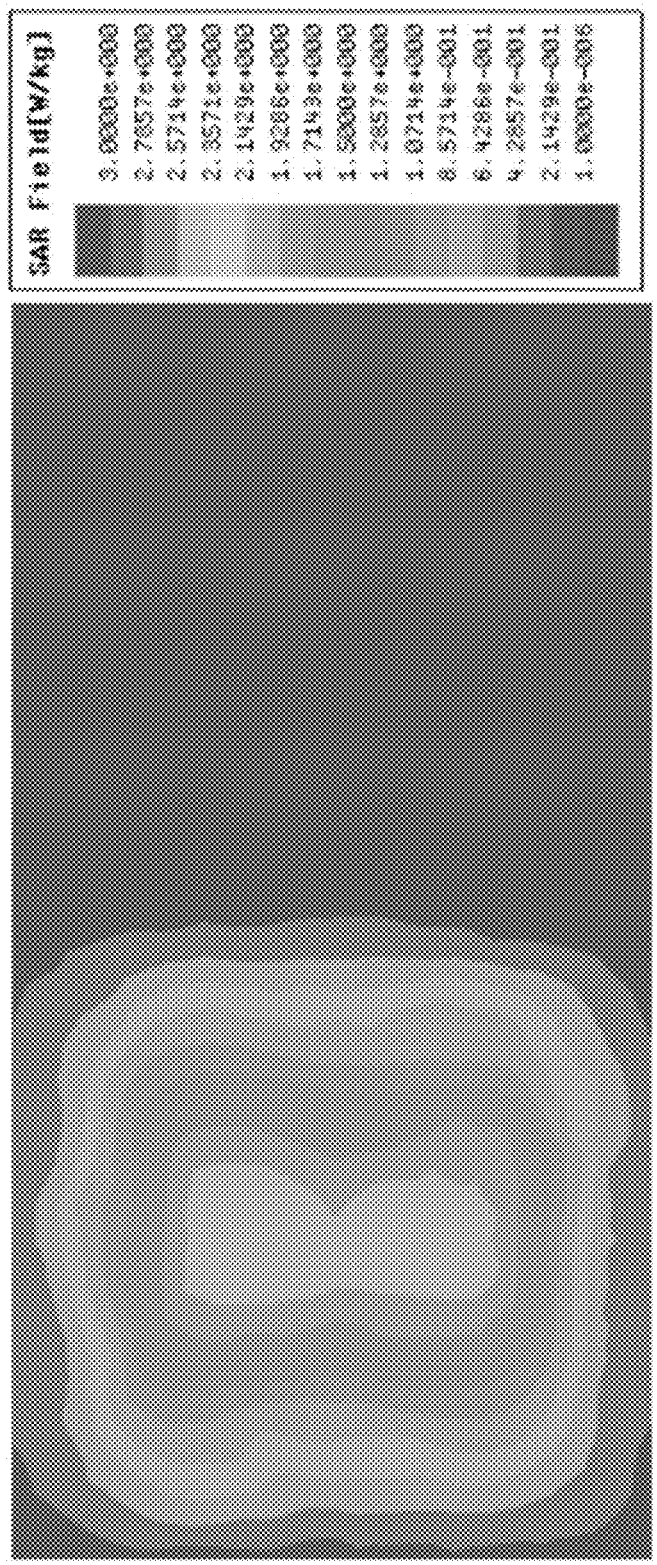
FIG. 9B shows a planar view of the simulated SAR pattern from the simulation illustrated in FIG. 7B.
Figure 10A:
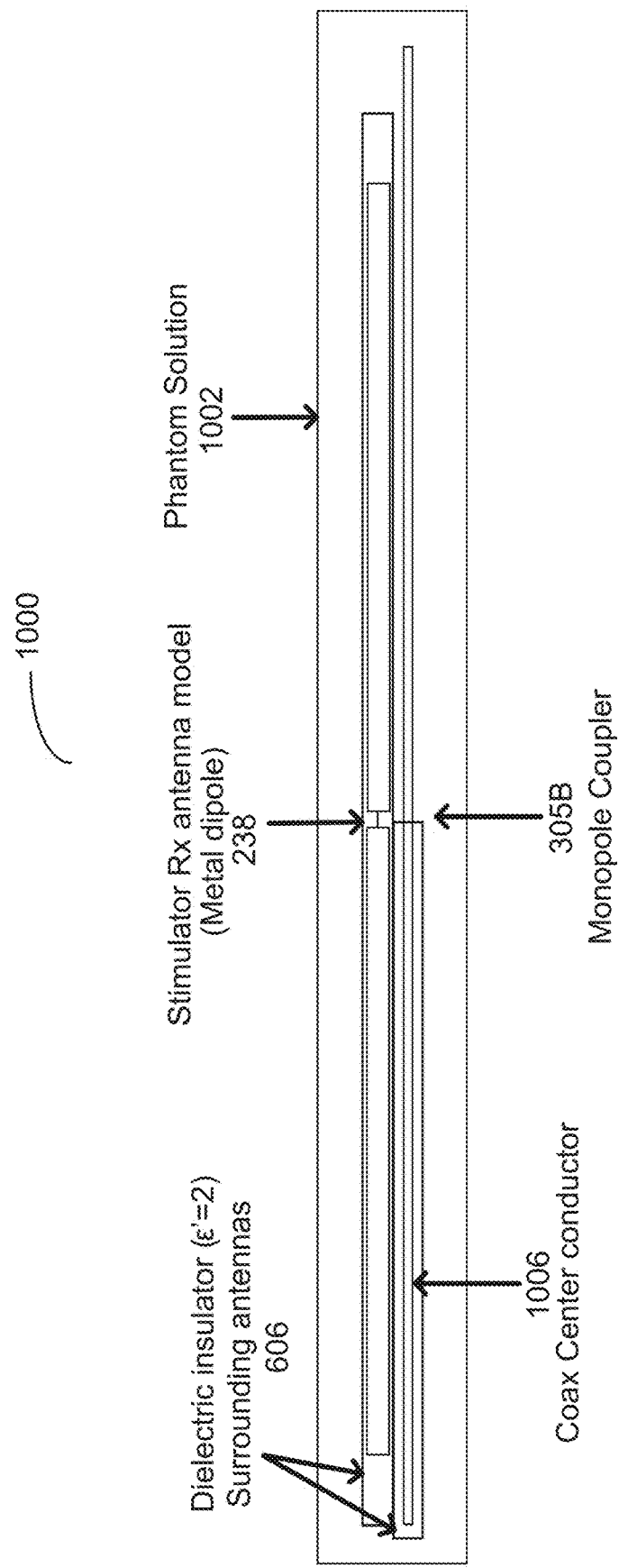
FIGS. 10A to 10F illustrate various views of an example of a relay module being coupled to the receiving antenna of an implantable stimulator device.
Figure 10B:
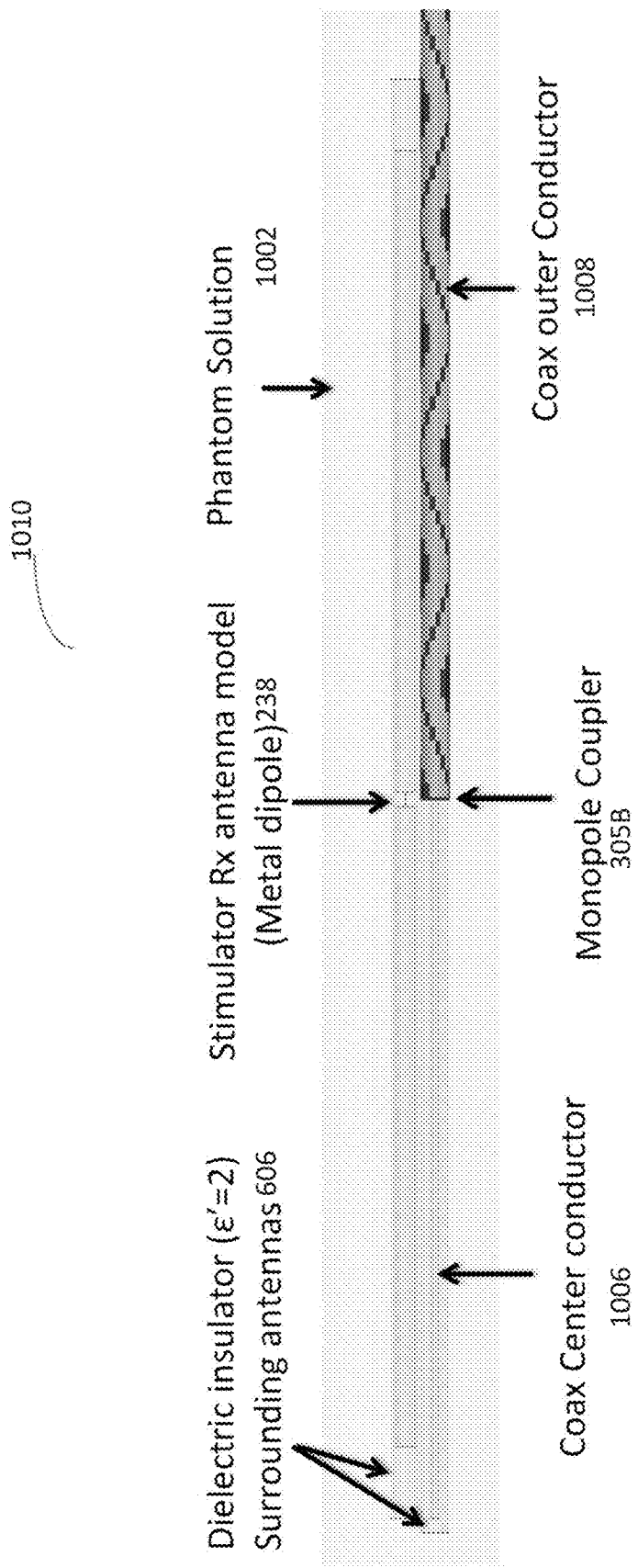
Figure 10C:
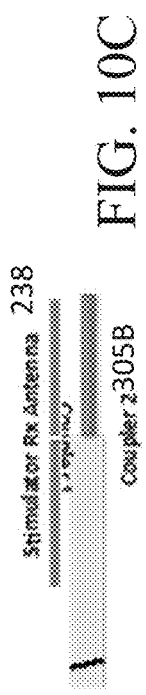
Figure 10D:
Figure 10E:
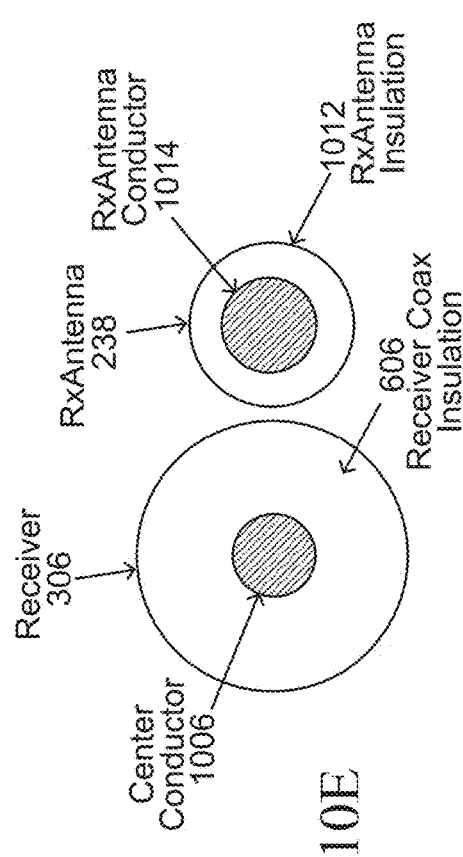
Figure 10F:
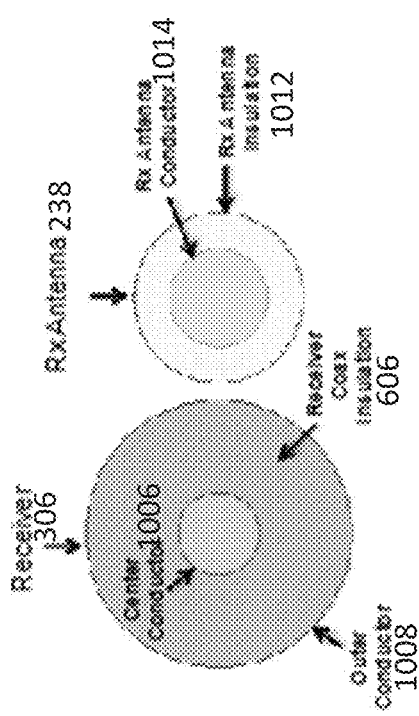

FIG. 8A shows an in-depth view of the simulated SAR pattern from simulation 700 as illustrated by FIG. 7A. In comparison, FIG. 8B shows an in-depth view of the simulated SAR pattern from simulation 710 as illustrated by FIG. 7B. Similarly, FIG. 9A shows a planar view of the simulated SAR pattern from simulation as illustrated by FIG. 7A. In comparison, FIG. 9B shows a planar view of the simulated SAR pattern from simulation 710 as illustrated by FIG. 7B. These planar views represent the view from 3 mm underneath the skin.

These SAR results are presented on a scale clamped at maximum of 10 W/kg. The contours are in log scale so the lower SAR levels at the ends of the relay module 306 and stimulator can be observed. As demonstrated, the relay module 306 and stimulator 308 can redistribute some energy along the length of the conductors, and some buildup of field can be observed at the ends of the outer conductor of relay module 308. This buildup can manifest as an increase in SAR surrounding the ends of the outer conductor of the relay module 306, which are not present in FIGS. 8B and 9B (when relay module 306 is not present in the simulation). Other than at the two ends of the outer conductor of the relay module 306, the SAR levels along the conductors are lower than the highest levels of SAR produced by the transmitting antenna 110 when relay module 306 and stimulator device 308 are absent.

Specifically, SAR buildup in the presence of relay module 306 and stimulator device 308 may occur when relay module 306 is aligned with the principal electric field and at a shallow depth of 3 mm, shown in FIG. 8B. The hot spots are at the ends of the relay module 306's outer conductors.

FIGS. 9A and 9B show the average SAR at the plane 3 mm below the skin surface. Generally, a relatively uniform incident field illumination is demonstrated. The relay module 306 will redistribute the field, resulting in some hot spots in FIG. 9B. As the relay module 306 is moved deeper inside, the incident field of the TX antenna 110 is attenuated. The SAR increase is due to the redistribution of incident field by relay module 306 becomes less significant. When the relay module 306 is in the RF field, it will redistribute the incident field, causing spots of higher concentration of field near the ends of outer conductor region of the relay module 306.

FIGS. 10A-10F illustrate various views of an example of a relay module 306 being coupled to the receiving antenna 238 of an implantable stimulator device 114. In particular, these figures illustrate a monopole coupler arm 305B, coax center conductor 1006, coax outer conductor 1008, as well as dielectric insulator surrounding receiving antenna 238 and coax center conductor 1006. These views emphasize the coupling from the monopole coupler arm 305B to the receiving antenna 238.

A number of implementations have been described. Nevertheless, it will be understood that various modifications may be made. Accordingly, other implementations are within the scope of the following claims.

What is claimed is:

1. A passive implantable relay module, comprising:
a first coupler arm arranged along a longitudinal axis of the passive implantable relay module and configured to wirelessly receive electromagnetic energy radiated through non-inductive coupling from a transmitting antenna located outside a subject's body; and
a second coupler arm longitudinally arranged along the long axis of the passive implantable relay module and configured to wirelessly transfer electromagnetic energy through non-inductive coupling to a receiving antenna on a passive wireless neural stimulator device that has been implanted inside the subject such that the passive wireless neural stimulator device is wirelessly powered; and
a connector portion sized and shaped to connect the first coupler arm to the second coupler arm.

2. The passive implantable relay module of claim 1, wherein the connector portion comprises a first metal core that is sized and shaped to run a longitudinal length that is approximately a half wavelength of electromagnetic waves propagating thereon from the first coupler arm to the second coupler arm and along the longitudinal axis of the passive implantable relay module.

3. The passive implantable relay module of claim 1, wherein the connector portion comprises a first metal core that is sized and shaped to run a longitudinal length that is approximately multiples of half wavelength of electromagnetic waves propagating thereon from the first coupler arm to the second coupler arm and along the longitudinal axis of the passive implantable relay module.

4. The passive implantable relay module of claim 1, wherein the connector portion comprises a first metal core that is sized and shaped to run a particular longitudinal length such that electromagnetic energy that has arrived at the second coupler arm is no less than 50% of electromagnetic energy that has been received at the first coupler arm and along the longitudinal axis of the passive implantable relay module.

5. The passive implantable relay module of claim 1, wherein the connector portion comprises a first metal core and electromagnetic energy that has arrived at the second coupler arm is at least 10 times greater than when the first metal core is absent.

6. The passive implantable relay module of claim 1, wherein the connector portion is sized and shaped to have a diameter that is no bigger than 1.8 mm.

7. The passive implantable relay module of claim 6, wherein the connector portion comprises a first metal core and is sized and shaped to snake through a tubing with a lumen of 1.8 mm or under when the passive implantable relay is implanted inside the subject such that (i) the second coupler arm is placed substantially parallel to the receiving antenna on a passive implantable neural stimulator device and (ii) the second coupler arm is positioned to wirelessly transmit the electromagnetic energy, through non-inductive coupling, to the receiving antenna on the passive wireless neural stimulator device that has been implanted inside the subject, wherein the electromagnetic energy has arrived from the connector portion.

8. The passive implantable relay module of claim 1, wherein the connector portion comprises a first metal core, and a second metal core sized and shaped to run a longitudinal length comparable to that of the first metal core, and wherein a distal end of the first metal core and a proximal end of the second metal core are positioned to form a parallel overlap but without contacting each other such that when the connector portion is placed inside a magnetic field where the subject is taking an magnetic resonance scan, heating caused by electrical charges accumulated along the connector portion during the magnetic resonance scan is substantially reduced than otherwise.

9. The passive implantable relay module of claim 8, wherein the parallel overlap runs approximately a half wavelength of electromagnetic waves carrying the electromagnetic energy received at the first coupler arm and from the transmitting antenna located outside the subject's body.

10. The passive implantable relay module of claim 1, wherein the connector portion comprises a first metal core and the first metal core is made of gold-plated stainless steel.

11. The passive implantable relay module of claim 10, wherein the connector portion comprises a first dielectric coating surrounding at least portions of the first metal core and the first dielectric coating is made of PolyEtherEtherKetone (PEEK).

12. The passive implantable relay module of claim 1, wherein the connector portion comprises a first metal core, and a first dielectric coating surrounding at least portions of the first metal core, and is without an outer shield that is made of metal.

13. The passive implantable relay module of claim 1, wherein the connector portion comprises a first metal core, a first dielectric coating surrounding at least portions of the first metal core, and an outer shield that is made of metal, the outer shield enclosing at least portions of the first dielectric coating.

14. The passive implantable relay module of claim 1, wherein the first coupler arm includes a first center conductor region, wherein the second coupler arm also includes a second center conductor region.

15. The passive implantable relay module of claim 14, wherein the first center conductor region is aligned with the transmitting antenna such that linearly polarized electric field is captured by the first center conductor region.

16. The passive implantable relay module of claim 14, wherein the second center conductor region is aligned with the transmitting antenna such that linearly polarized electric field is captured by the second center conductor region.

17. The passive implantable relay module of claim 14, wherein the first center conductor region and the second center conductor region are of substantially identical length of approximately 5 mm.

18. The passive implantable relay module of claim 1, comprising a housing with an antenna lumen to enclose the first coupler arm, the connector portion, and the second coupler arm.

19. The passive implantable relay module of claim 1, comprising a housing with a stylet lumen to house a guiding device when the passive implantable relay module is being implanted.

20. A method of implanting a passive implantable relay module, the method comprising:
    implanting a passive implantable neural stimulator device inside a subject such that electrodes of the passive implantable neural stimulator device are positioned to deliver electric charges to excitable tissue;
    inserting a passive implantable relay module by snaking the passive implantable relay module through a tubing such that a distal coupler arm of the passive implantable relay module is placed substantially parallel to a receiving antenna on the passive implantable neural stimulator device; and
    placing a proximal coupler arm of the passive implantable relay module underneath the subject's skin such that (i) the proximal coupler arm is configured to receive electromagnetic energy wirelessly and through non-inductive coupling from an external radio frequency pulse generator module placed outside the subject when the external radio frequency pulse generator module is activated, and (ii) the distal coupler arm is configured to wirelessly transmit electromagnetic energy, again through non-inductive coupling, to the receiving antenna on the passive wireless neural stimulator device, thereby wirelessly powering the passive implantable neural stimulator device.

21. The method of claim 20, wherein inserting a passive implantable relay module comprises snaking the passive implantable relay module through a tubing on the passive implantable neural stimulator device.

\* \* \* \* \*